United States Patent [19]
Miller

[11] Patent Number: 6,086,584
[45] Date of Patent: Jul. 11, 2000

[54] CELLULAR SUBLIMATION PROBE AND METHODS

[75] Inventor: Gary H. Miller, Milpitas, Calif.

[73] Assignee: Ethicon, Inc., Somerville, N.J.

[21] Appl. No.: 09/151,015

[22] Filed: Sep. 10, 1998

[51] Int. Cl.[7] .................................................. A61B 18/14
[52] U.S. Cl. ................................ 606/41; 606/46; 606/49; 604/114; 607/99; 607/105; 607/113
[58] Field of Search .................................. 606/41, 45, 46, 606/49; 604/114; 607/99, 105, 113

[56] References Cited

U.S. PATENT DOCUMENTS

| | | | |
|---|---|---|---|
| 5,569,242 | 10/1996 | Lax et al. ..................................... | 606/42 |
| 5,681,282 | 10/1997 | Eggers et al. ............................ | 604/114 |
| 5,697,882 | 12/1997 | Eggers et al. ............................ | 604/114 |
| 5,944,715 | 8/1999 | Goble et al. ............................... | 606/41 |

*Primary Examiner*—Lee Cohen
*Attorney, Agent, or Firm*—Verne E. Kreger, Jr.

[57] ABSTRACT

The invention provides exemplary electrosurgical probes and methods for their use. In one exemplary embodiment, an electrosurgical probe comprises a probe body having a proximal end, a distal end and at least one lumen. An electrode assembly is operably coupled to the distal end. The electrode assembly includes an electrode and a jacket disposed to cover at least a portion of the electrode. The jacket and the electrode have a combined mass sufficient to dissipate heat during operation of the electrode so that the electrode does not experience material degradation. Further, the jacket provides insulation between the electrode and a conductive medium such that the electrode is operable in the conductive medium.

25 Claims, 5 Drawing Sheets

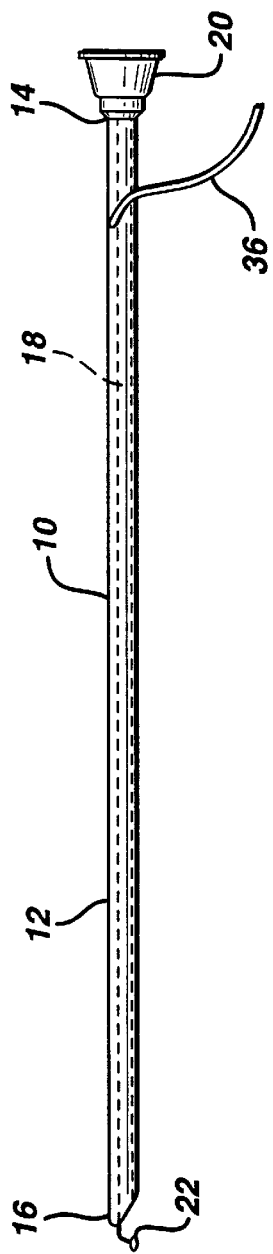
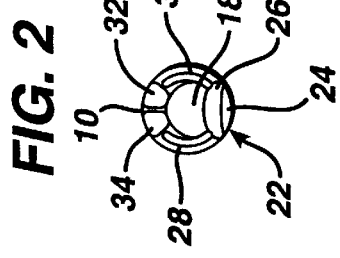
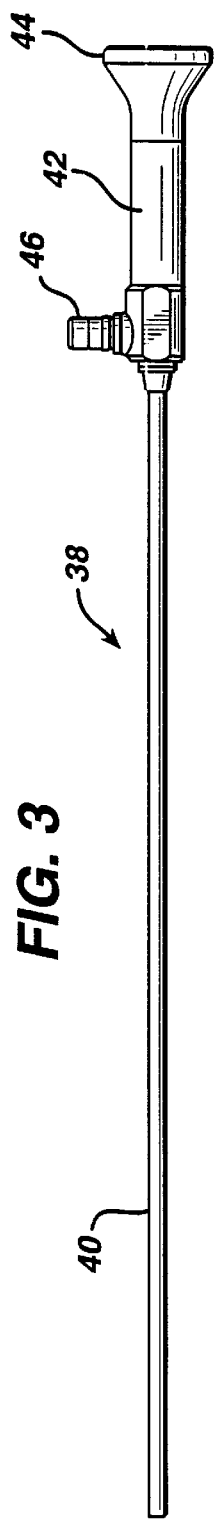
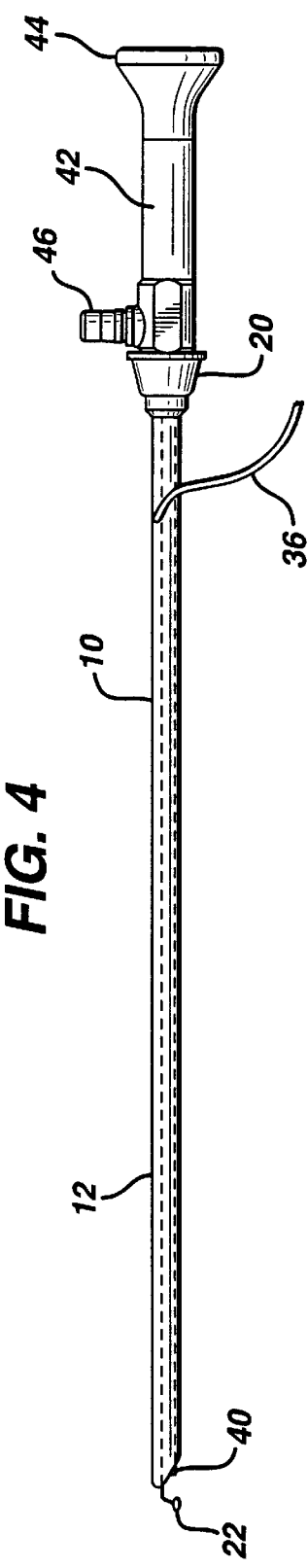
FIG. 1
FIG. 2
FIG. 3
FIG. 4

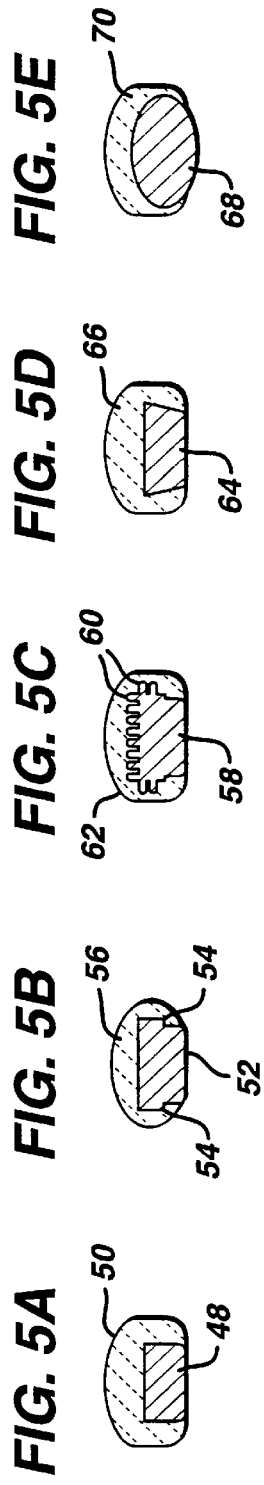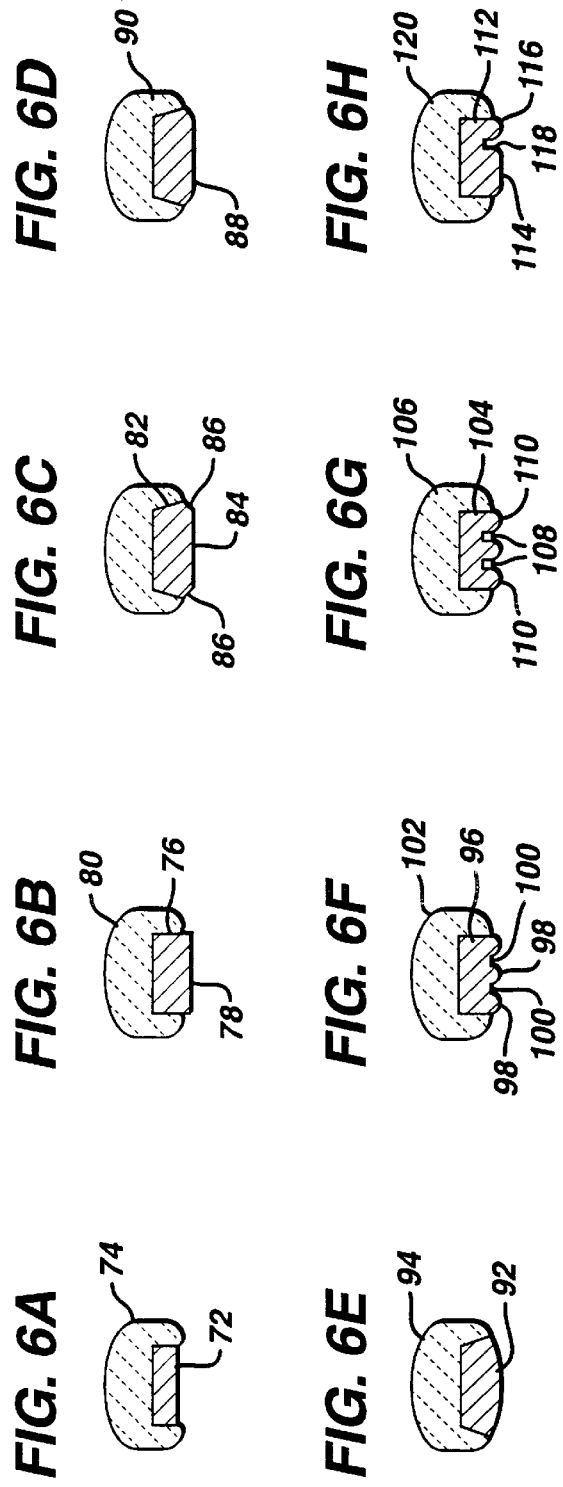

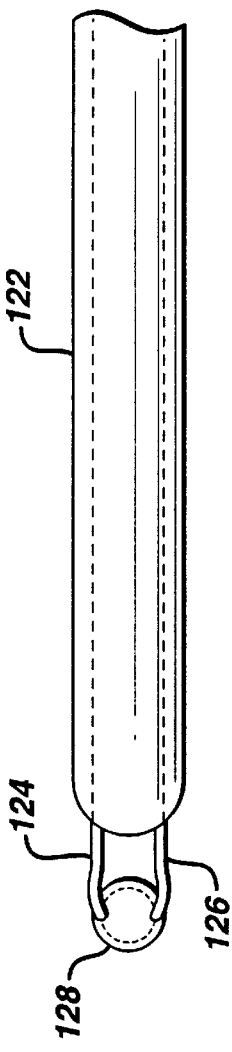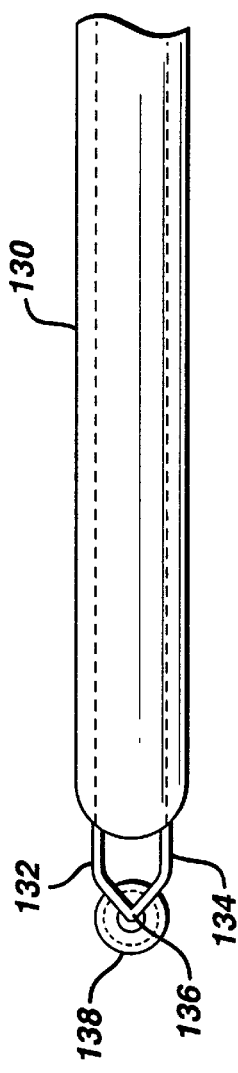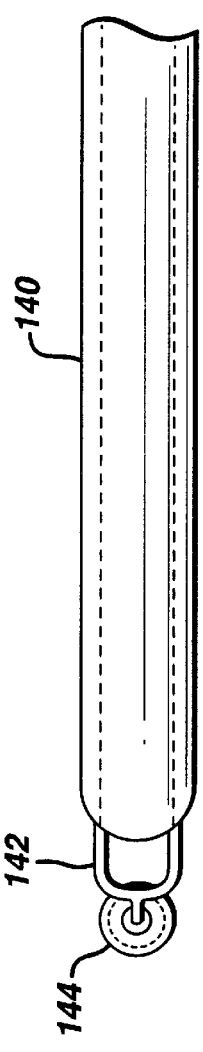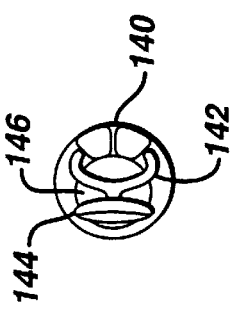

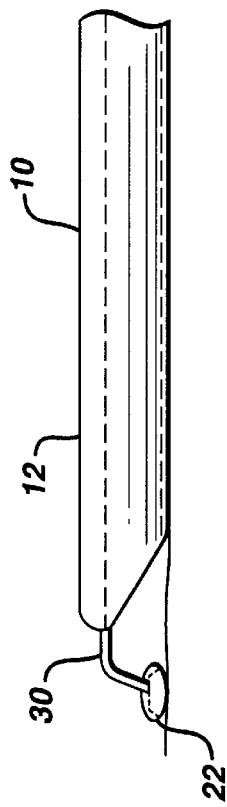
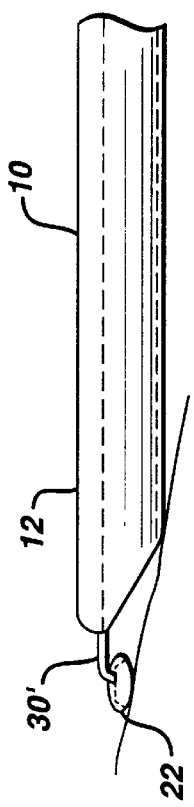
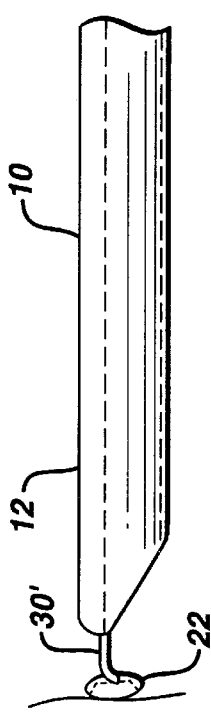
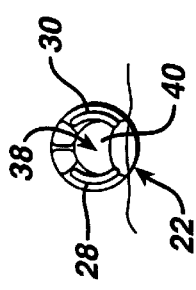
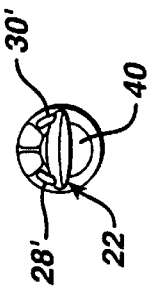
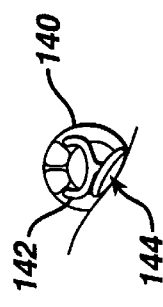

CELLULAR SUBLIMATION PROBE AND METHODS

BACKGROUND OF THE INVENTION

The invention relates generally to the field of electrosurgery, and in particular to electrosurgical procedures which are performed within a body cavity which is filled with a liquid. In one particular aspect, the invention relates to the vaporization and cauterization of tissue in a body cavity which is filled with a conductive medium.

Electrosurgical devices are currently being used to treat a variety of ailments. For example, electrosurgical devices are successfully being used to cut and ablate tissue, as well as to provide coagulation. One exemplary electrosurgical device that is useful in treating the endometrial lining of the uterus (among other applications) is described in U.S. Pat. No. 5,456,689 and in U.S. application Ser. No. 08/322,680, filed Oct. 13, 1994, now abandoned, the disclosures of which are herein incorporated by reference. One embodiment described in U.S. Pat. No. 5,456,689 includes a wire loop electrode that may be used to cut tissue when current is supplied to the electrode and the electrode is moved through tissue.

In some circumstances it may be desirable to perform electrosurgical procedures in locations that are filled with an electrically conductive medium. For example, co-pending U.S. patent application Ser. No. 08/678,412, filed Jul. 2, 1996; Ser. No. 08/822,901, filed May 20, 1997; and Ser. No. 09/046,298, filed Mar. 23, 1998 describe exemplary electrosurgical devices and methods for treating tissue in an environment having an electrically conductive medium. The complete disclosures of all these references are herein incorporated by reference.

While the above referenced electrosurgical devices have proven to be extremely successful, it is desirable to provide other electrosurgical devices for other applications and treatments. In one aspect, it would be desirable to provide an electrosurgical device which can be used at high power settings to vaporize tissue and provide coagulation effects. Such a device should have an electrode which is durable and robust so that it will not materially degrade when used at high power settings. Further, it would be desirable if such a device were useful in either a conductive or a non-conductive medium. In another aspect, it would be desirable to provide an electrosurgical device that is useful on an outpatient basis so that tissue may be treated without requiring a prolonged stay in a healthcare facility. In still another aspect, it would be desirable to provide a device with a relatively large electrode so that larger areas of tissue may be treated in a more efficient manner.

SUMMARY OF THE INVENTION

The invention provides exemplary electrosurgical probes and methods for their use. The probes of the invention are particularly useful in vaporizing or cauterizing tissue, particularly within a physiologic (conductive) distention medium, although the probes are also useful in non-conductive media. In one exemplary embodiment, an electrosurgical probe is provided which comprises a probe body having a proximal end, a distal end and at least one lumen. An electrode assembly is operably coupled to the distal end, with the electrode assembly comprising an electrode and a jacket disposed to cover at least a portion of the electrode. The jacket and the electrode have a combined mass that is sufficient to dissipate heat produced during operation of the electrode so that the electrode does not experience material degradation. Further, the jacket provides insulation between the electrode and a conductive medium such that the electrode is operable within the conductive medium.

The electrode is preferably constructed of a metal or metal alloy, while the jacket is preferably constructed of a ceramic material. In one particularly preferable aspect, the jacket and the electrode have a combined mass that is greater than about 0.04 gram, and more preferably, in the range from about 0.1 gram to about 0.2 gram. Such a combined mass allows for the electrode assembly to be operated at relatively high power settings without materially degrading the electrode. For instance, when the jacket and the electrode have such a combined mass, the heat that is produced during an electrosurgical procedure may be effectively dissipated by the electrode assembly without causing degradation to the electrode.

In another aspect, the electrode preferably has an exposed surface area that is in the range from about 0.07 $in^2$. to about 0.125 $in^2$. Such a surface area is particularly useful in allowing the electrode assembly to be effectively used in vaporizing or cauterizing tissue.

In still another aspect, the probe body has a working lumen, a fluid inflow lumen, and a fluid outflow lumen. In this way, the inflow and outflow lumens may be used to introduce distention or other media as well as to enhance visual clarity of the hollow viscus. In one particular aspect, the probe body has an outer diameter that is in the range from about 0.07 inch to about 0.3 inch. Such an outer diameter is particularly useful in that the probe may be inserted into a variety of commercially available sheaths. Further, the probe diameter is smaller than or equal to the natural inner cervical diameter, thereby facilitating atraumatic introduction and implementation.

In another particular aspect, the electrode assembly is coupled to the distal end with a fixed mount such that the position of the electrode assembly relative to the probe body is fixed. Alternatively, the electrode assembly may be coupled to the distal end with a movable mount such that the electrode assembly is movable relative to the probe body. Use of such a movable mount allows substantially all of the area of the electrode to be consistently maintained in contact with the wall of the body cavity, thereby minimizing procedure time.

The electrosurgical probe as described above may be included as part of an electrosurgical system which includes an imaging scope that is receivable in the working lumen of the probe body. In this manner, the tissue to be treated may be visualized during the treatment process. The working lumen preferably has a diameter in the range from about 0.03 inch to about 0.16 inch. Such a diameter allows for the introduction, of a variety of imaging scopes, such as flexible fiberscopes, rigid telescopes, and the like.

The electrosurgical system includes an electrosurgical unit to supply current to the active electrode. A source of conductive fluid is also provided which is connectable to the fluid inflow lumen to introduce an electrically conductive distention medium into the body cavity. A vacuum source is also provided and is connectable to the fluid outflow lumen to withdraw fluids from the body cavity to improve the visualization during a procedure.

The invention further provides a method for electrosurgically treating tissue. According to the method, an electrosurgical probe is provided which comprises a probe body having a proximal end, a distal end, at least one lumen, and an electrode assembly operably coupled to the distal end. The electrode assembly in turn comprises an electrode and a jacket disposed to cover at least a portion of the electrode. The probe is introduced into a body cavity, and a conductive medium is introduced into the cavity through the lumen. Current is then supplied to the electrode, and the electrode is positioned near or against tissue to treat the tissue. As the electrode is activated, the jacket provides insulation between the electrode and the conductive medium. Further, heat produced during treatment of the tissue is dissipated by the jacket and the electrode to prevent the electrode from materially degrading.

To vaporize or cauterize tissue, the electrode is preferably operated at a power setting that is in the range from about 86 watts to about 300 watts. In one aspect, the probe body further includes a working lumen, and an imaging scope is introduced into the working lumen to visualize the position of the electrode within the body cavity. The probe body preferably also includes an aspiration lumen to allow the conductive medium to be withdrawn from the body cavity to improve the field of vision. In still another aspect, the electrode assembly is pivotally coupled to the distal end so that as the electrode is moved along tissue, the electrode assembly will pivot to accommodate the shape of the tissue.

BRIEF DESCRIPTION OF THE DRAWINGS

FIG. 1 is a side view of an exemplary electrosurgical device according to the invention.

FIG. 2 is an end view of the device of FIG. 1.

FIG. 3 is a side view of an imaging scope that may be used with the device of FIG. 1 according to the invention.

FIG. 4 illustrates the scope of FIG. 3 inserted into the device of FIG. 1.

FIG. 5 is a top view of a distal portion of the device of FIG. 1.

FIGS. 5A–5E are cross sectional views showing various embodiments of electrode assembly configurations according to the invention.

FIGS. 6A–6F are cross sectional views showing various electrode configurations according to the invention.

FIG. 7 illustrates an electrode assembly coupled to a probe body with a single axis swivel mount according to the invention.

FIG. 8 illustrates an electrode assembly coupled to a probe body with a two axis swivel mount that is joint supported according to the invention.

FIG. 9 illustrates an electrode assembly coupled to a probe body with a two axis swivel mount that is strut supported according to the invention.

FIG. 10 is an end view of the probe body and the electrode assembly of FIG. 9.

FIG. 11 illustrates the electrosurgical device of FIG. 1 being used to vaporize tissue according to the invention.

FIG. 12 is a front view of the device of FIG. 11 when vaporizing tissue.

FIG. 13 illustrates the electrosurgical device of FIG. 1 with a larger sized electrode that is aligned with an imaging lumen while vaporizing tissue according to the invention.

FIG. 14 is a front view of the device of FIG. 13.

FIG. 15 illustrates the electrosurgical device of FIG. 13 showing the swivel motion of the electrode to allow the electrode to vaporize tissue which is situated at various angles relative to the device according to the invention.

FIG. 16 illustrates the electrode assembly and probe body of FIG. 10 when vaporizing tissue according to the invention.

DETAILED DESCRIPTION OF THE SPECIFIC EMBODIMENTS

Figure 18:
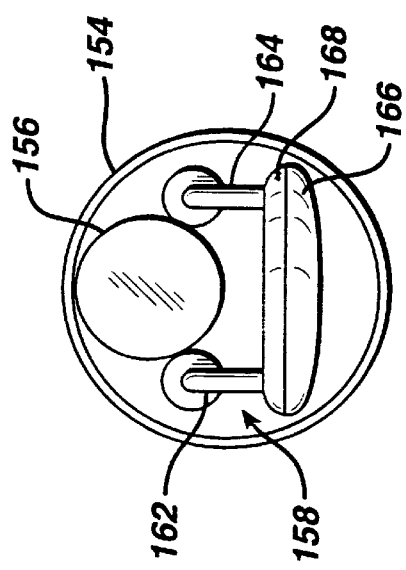
FIG. 18 is a front view of the device of FIG. 17.

The invention provides exemplary electrosurgical probes, electrosurgical systems, and methods for their use. The probes of the invention are particularly useful in sublimating or vaporizing tissue. The probes of the invention include a relatively large electrode that may be operated at relatively high power settings to create an arc which, when contacting tissue, causes the cells to rupture, thus vaporizing the tissue. Although primarily useful in vaporizing tissue, the probes of the invention may also be used to cauterize tissue.

The probes of the invention preferably comprise a semi-rigid or flexible body having an active electrode at a distal end and a single or multiple port connection on the proximal end. The probe body preferably has a length in the range from about 4 inches to about 24 inches, and more preferably at about 12 inches, for applications within the uterine cavity.

The active electrode at the distal end preferably has a disc or spherical shape and is coupled to the probe body such that the active surface of the electrode may be positioned in the direction of, and in apposition to, the ablatable tissue. The opposing side of the electrode is preferably covered with a dielectric refractory material, such as a ceramic material, a high temperature polymer, such as Teflon, glass, glass former, and the like. The dielectric refractory material is particularly advantageous in that it dissipates heat produced during ablation. Moreover, the material acts as an insulation layer between the physiologic distention media and the active electrode.

As just mentioned, the probe is preferably used within a hollow viscus that is filled or distended with a physiologic, i.e., conductive, distention media. Exemplary conductive media include normal saline solutions, lactated Ringer's solutions, and the like. Use of such solutions are advantageous in that the normal cellular sodium concentration may be maintained during the procedure so as not to disrupt hemostasis. Although particularly useful in physiologic distention media so as not to disturb the sodium balance (hyponatremia), it will be appreciated that the probes of the invention may also be used with non-conductive distention media as well, including sorbitol, mannitol, glycine, and the like.

Although the probes of the invention will find their greatest use in treating tissue within the uterine cavity, the probes may be used within any hollow viscus, including the prostate, and the like. In one particular embodiment, the outer profile of the probe is minimized so that it may be introduced into the uterine cavity with minimal cervical dilation and trauma.

The probe body may include one or more lumens, of which one preferably allows the passage of an imaging scope. Other lumens may be used to communicate hydraulically between the proximal connection and the distal end, thereby allowing the introduction of distention and visualization media. Other lumens may be used to move other fluids into or out of the body cavity and to allow for the passage of various other devices. The connection at the proximal end is preferably used to couple the imaging scope to the sublimating probe body.

Construction of the probes of the invention provide a number of design advantages. For example, the electrode preferably has a relatively large size which allows for operation at high electrosurgical power settings without material degradation. For example, the electrode may be operated at power settings in the range from about 40 watts to about 400 watts to vaporize tissue. The electrode and dielectric jacket preferably have a combined mass than is greater than about 0.04 gram, and more preferably in the range from about 0.1 gram to about 0.2 gram. Such a mass is sufficient so that the electrode will be able to withstand the relatively high power settings without material degradation.

The ceramic jacket is further advantageous in that it allows for the electrode to be operated in physiologic distention media. The ceramic jacket serves as an insulator so that the current may concentrate at the non-insulated surface areas of the electrode which are to be placed in contact with or in apposition to the ablatable tissue. If such a jacket were not employed, the current would disperse equally throughout the conductive media, thereby reducing the current concentration in the regions which are used to vaporize the tissue.

A further advantage of the probes of the invention is that the working lumen allows for the passage of various devices into the body cavity, including imaging scopes, biopsy tools, fluids, and the like. The inflow and outflow lumens also allow for the delivery of fluids, such as radiopaque fluids, drugs, imaging media, distention media, and the like, into the body cavity.

Still another advantage is that the probe body may be constructed to have a relatively small outer diameter which is compatible with most commercially available sheaths. Preferably, the probe body has an outer diameter in the range from about 0.07 inch to about 0.30 inch. If the probe body includes only a central working lumen, the outer diameter may be made especially small to facilitate its introduction into small body cavities. Moreover, by employing a flexible fiberscope as the imaging device, the outer diameter of the probe body may be kept at a minimum. As an example, the scope lumen may have a diameter in the range from about 0.03 inch (for fiberscopes) to about 0.16 inch (for rigid telescopes). In this way, the scope lumen may be adapted to receive a variety of commercially sized imaging devices, such as 1–4 mm fiberscopes, 2.7 mm telescopes, 4.0 mm telescopes, and the like. Further, the connection at the proximal end may be configured to have a mount type which is compatible with the most domestic and international scope brands, such as Circon, Storz, Wolf, and the like.

Another particular design advantage of the probes of the invention is that the electrode assembly may either be fixedly or movably attached to the probe body. Such configurations allow for electrode maneuverability with respect to the probe body so that the probe may be employed to effectively treat tissue having a variety of shapes and configurations.

The design advantages described above provide the probes of the invention with a variety of clinical advantages. For example, for cases within the uterus, the probe diameter is smaller than or equal to the natural inner cervical diameter. In this way, the probe may be introduced into the uterus and then operated in an atraumatic manner. The small probe dimensions also enable physicians to perform myoma treatment in office settings in an outpatient manner. In this way, procedures which are now typically performed within a hospital may be performed in an outpatient manner, thereby significantly reducing the costs to the patient.

Another clinical advantage is that the probe may be introduced and positioned at a desired location under direct vision using flexible or rigid scopes. In this manner, orientation and navigation of the probe may be optimized.

As described above, the apposition of the electrode with tissue may be maintained due to the maneuverability of the electrode. In this way, a variety of tissue surfaces may be effectively vaporized without the need for reorienting the probe body, thus minimizing procedure time. To provide maneuverability to the electrode, the electrode may be pivotally mounted to the probe body to provide either single or double axis electrode swivel action. Such configurations allow substantially the entire active area of the electrode to be consistently maintained in contact with the surface of the body cavity, thereby minimizing procedure time.

Procedure time is also minimized due to the large area "high current density" electrode which delivers energy to a large surface area. By being able to vaporize large areas of tissue, operation time is minimized. In one particular aspect, the exposed surface area of the electrode is preferably in the range from about 0.007 $in^2$. to 0.125 $in^2$.

The use of inflow and outflow lumens provides distention capabilities and also enhances the visual clarity of the hollow viscus. In a further clinical advantage, a variety of electrode configurations may be provided as discussed below to allow for cellular vaporization as well as combined coagulative effects.

Referring now to FIGS. 1 and 2, an exemplary embodiment of an electrosurgical device 10 will be described. Device 10 comprises an elongate probe body 12 having a proximal end 14 and a distal end 16. A working lumen 18 extends between the proximal end 14 and distal end 16. Probe body 12 may be constructed to be either semi-rigid or flexible, with preferable materials for constructing probe body 12 comprising polymers, such as polyolefins, polyesters, nylons and the like. Coupled to proximal end 14 is a scope mount 20 to which an imaging scope may be coupled as described in greater detail hereinafter. Coupled to distal end 16 is an electrode assembly 22. As best shown in FIG. 2, electrode assembly 22 comprises an electrode 24 and a jacket 26. A pair of arms 28 and 30 couple electrode assembly 22 to distal end 16. Electrode 24 is preferably constructed of a metal or metal alloy and is employed to produce an electrical spark to vaporize or cauterize tissue. Jacket 26 is preferably constructed of a dielectric material, such as ceramic, which serves to dissipate heat created during vaporization and to insulate a portion of electrode 24 from an electrically conductive medium.

Probe body 12 further includes a fluid inflow lumen 32 and a fluid outflow lumen 34. Conveniently, a connector tube 36 is coupled to inflow lumen 32 to allow fluids to be introduced into the body cavity. Although not shown, a similar tube is connected to outflow lumen 34 so that fluids may be withdrawn from the body cavity. In this way, various distention or imaging media may be introduced into the body cavity to distend the body cavity or to clear fluids to improve visualization.

Referring now to FIG. 3, an exemplary imaging scope 38 which may be inserted through working lumen 18 of probe body 12 (see FIGS. 1 and 2) will be described. Imaging scope 38 comprises an elongate shaft 40 which may include fiberscopic bundles or other optics associated with commercially available telescopes. In this way, shaft 40 may be constructed to be either flexible or rigid. Coupled to shaft 40 is a housing 42 which includes an eyepiece 44 and a light coupling 46 to allow a light source to be coupled to housing 42. As is known in the art, imaging scope 38 may comprise any one of a variety of commercially available scopes, including 2.7–4.0 mm rigid telescopes, 1.6 mm flexible fiberscopes and the like.

As illustrated in FIG. 4, shaft 40 is insertable through working lumen 18 until housing 42 is coupled with scope mount 20. In this way, a hydrostatic seal is provided between scope 38 and device 10 to allow the body cavity to be distended while preventing liquid from leaking from working lumen 18. Moreover, when scope 38 is coupled to device 10, electrode assembly 22 may be visualized, both during introduction of device 10 into a body cavity as well as during an electrosurgical procedure where electrode 24 is employed to vaporize or cauterize tissue.

In an exemplary procedure, the inner lining of the uterine cavity may be treated by first introducing a sheath through the cervical canal to provide access to the uterine cavity as is known in the art. Scope 38 is then inserted through working lumen 18 and the combined scope 38 and device 10 are inserted through the sheath to gain access into the uterine cavity. A distention medium is then introduced through tube 36 and into fluid inflow lumen 32 to distend the uterus, preferably with a physiologic distention media. If needed, fluids may be withdrawn through fluid outflow lumen 34 to improve the visibility within the uterine cavity. At any time, visualization of electrode assembly 22 may be gained by looking through eyepiece 44. When situated to vaporize tissue, electrosurgical current is provided to electrode 24 which is placed in apposition to the desired tissue.

To prevent any of the pressurized fluid from leaking between the sheath and device 10, proximal end 14 preferably includes a housing having a tapered portion which mates with and provides a seal with the hub of the sheath. In this way, device 10 may be used with essentially any type of standard or commercially available sheath. If device 10 needs to be translated within the sheath, a distensible O-ring may be fitted to the outer diameter of device 10 to provide hydro-stasis. Device 10 is preferably constructed to have a length that exceeds the length of standard sheaths so that distal end 16 will extend beyond the tip of the sheath.

In some cases, the fluid may be introduced into the body cavity through a fluid inflow lumen in the sheath. In this way, fluid inflow lumen 32 may be eliminated. In this manner, the overall size of device 10 may be reduced for profile optimization and device performance.

FIG. 5 illustrates a top view of an electrode assembly 47 in schematic form. A section line 49 is provided to illustrate the orientation of FIGS. 5A–5E (which illustrate various embodiments of electrode assembly designs). The embodiments illustrated in FIGS. 5A–5E are shown to illustrate the various ways in which the jacket may be coupled to the electrode to provide exemplary heat transfer characteristics so that heat produced during the vaporization procedure may be effectively dissipated so as not to materially degrade the electrode. As shown in FIG. 5A, a generally rectangular electrode 48 is surrounded on three of its sides by a ceramic jacket 50. In FIG. 5B, an electrode 52 includes a pair of steps 54 that may be locked with a ceramic jacket 56 having an elliptical outer surface. In FIG. 5C, an electrode 58 is provided with a plurality of fingers 60 which serve as heat sinks to facilitate the transfer of heat from electrode 58 to a jacket 62. FIG. 5D shows an electrode 64 having a wedge shape to key with a jacket 66. Finally, FIG. 5E shows an elliptical electrode 68 which is keyed with a ceramic jacket 70 to lock electrode 68 relative to jacket 70.

Hence, the electrode configuration shown in FIGS. 5A–5E are provided to enhance the heat transfer from the electrodes to the jackets so that the electrode will not materially degrade during a vaporizing procedure. The various electrode assemblies may be manufactured by any one of a variety of processes. For example the electrodes may be mill machined, EDM machined, coined, forged, cast, and the like. The jackets may be formed by mill machining, metal oxide spraying, dip coating, electrostatic deposition, chemical deposition, vapor deposition, and the like.

Referring now to FIGS. 6A–6F, further electrode assembly designs will be described. The embodiments of FIGS. 6A–6F are provided to illustrate different active surface area configurations to enhance the treatment of tissue. Although not shown, it will be appreciated that any of the elements of the embodiments described in FIGS. 5A–5E may be incorporated into the embodiments illustrated in FIGS. 6A–6F and vice versa. In FIG. 6A, a generally rectangular electrode 72 is recessed within a jacket 74. In this manner, a fulguration recess is provided so that tissue may be fulgurated without directly contacting electrode 72 with tissue.

In FIG. 6B, an electrode 76 has a generally planar surface 78 which projects from a jacket 80. In this way, planar surface 78 serves as a vaporizing surface, with the corners adjacent planar surface 78 serving to concentrate the current to provide high-energy edges may be employed to both vaporize and cut tissue.

In FIG. 6C, an electrode 82 has a protruding vaporizing surface 84 with high energy planes 86 where current tends to concentrate. In this way, high energy planes 86 may be used to more effectively vaporize or ablate tissue. In FIG. 6D, an electrode 88 and a jacket 90 are shown which are similar to the embodiment of FIG. 6C except that electrode 88 and jacket 90 have a greater mass to enhance heat transfer to reduce the chances of materially degrading electrode 88 during a vaporization procedure.

In FIG. 6E, an electrode 92 has a curved active surface which is useful in performing procedures involving both vaporization and cauterization. Electrode 92 is surrounded by a jacket 94 and include no high energy edges. As such, electrode 92 may be used to perform functions similar to a standard roller-ball or roller-barrel type electrode. In FIG. 6F, an electrode 96 has a plurality of lobes 98 where current tends to concentrate to more effectively vaporize the tissue. Fulguration surfaces 100 are provided between lobes 98 to fulgurate tissue while lobes 98 are vaporizing tissue. Electrode 96 is disposed within a jacket 102. In FIG. 6G, an electrode 104 and jacket 106 are essentially identical to those in FIG. 6F except for the addition of a dielectric material 108 which is disposed between lobes 110. In this way, a multi-lobe electrode surface is provided. In FIG. 6F, an electrode 112 has a vaporizing/coagulation surface 114 and a lobe 116. A dielectric material 118 is disposed between surfaces 114 and 116. The jacket 120 is disposed about electrode 112.

It will be appreciated that the various embodiments illustrated in FIGS. 5A–5E and 6A–6F are not exhaustive.

Indeed, a wide variety of electrode surfaces and heat transfer designs may be provided to enhance the functionality of the electrode assembly. For example, the electrode surfaces may be recessed, planar, lobed, spherical, conical, cylindrical, triangular, multi-surfaced, combined planar/lobed, and the like. By providing various electrode configurations, a treatment system having a wide assortment of electrode configurations may be provided at a relatively small cost and used during the same procedure. For example, one device may have an electrode with edges and may be used to provide high-energy vaporization and "cutting/ablating". This device may quickly be swapped with another device having an electrode which provides for pure "high efficiency" coagulation.

As previously described, the electrode assemblies of the invention may be fixedly mounted relative to the probe body or may be pivotally or swivel-mounted relative to the probe body to provide multiple degrees of rotational freedom. For example, FIG. 7 illustrates a probe body 122 having a pair of arms 124 and 126 to which an electrode assembly 128 is hingedly mounted. In this way, electrode assembly 128 may swivel about an axis extending between arms 124 and 126. In FIG. 8, a probe body 130 includes a pair of arms 132 and 134 which are joined together at a point 136. An electrode assembly 138 is swivel-mounted to point 136, such as with a ball and socket arrangement. In this way, electrode assembly 138 may pivot to provide multiple degrees of freedom of movement. In FIGS. 9 and 10, a probe body 140 includes a strut arrangement 142 to which an electrode assembly 144 is swivel-mounted in a manner similar to the embodiment of FIG. 8. In this manner, electrode assembly 144 may swivel about multiple degrees of freedom. As shown in FIG. 10, use of strut arrangement 142 is particularly advantageous in that it, increases the field of view from a scope 146.

In addition to the fixed mountings or rotational mountings as just described, the electrode assemblies may be mounted relative to the probe bodies so that they are either aligned with or eccentric to the field of vision provided by the scope. For example, FIGS. 11 and 12 illustrate the electrosurgical device of FIGS. 1 and 2 when vaporizing tissue. Electrode assembly 22 is positioned at a bottom portion of the field of view of scope 38 as illustrated in FIG. 12 so that the electrode assembly is eccentric to the image. In this way, the physician may view above and beyond the tissue being vaporized. Electrode assembly 22 may be either fixedly or pivotally mounted to arms 28 and 30 to provide various degrees of rotational freedom when the electrode assembly is placed in apposition to tissue.

Shown in FIG. 13 is electrosurgical device 10 having modified arms 28' and 30' so that electrode assembly 22 is aligned with the field of vision of probe 38. Such a configuration is particularly advantageous for tissue which is at an angle relative to probe body 12 as illustrated in FIG. 13. Another advantage of positioning electrode assembly 22 along a central axis of device 10 is that the active electrode may be constructed to have a larger surface area.

FIG. 15 illustrates device 10 having modified arms 28' and 30' and with electrode assembly 22 being pivotally attached to arms 28' and 30'. In this way, electrode assembly 22 may be swivelled perpendicular to the axis of probe body 12 as shown. Such a configuration is particularly advantageous in treating tissue distal and perpendicular to the central axis of the device.

FIG. 16 illustrates probe body 140 and electrode assembly 144 of FIGS. 9 and 10 when used to treat tissue which is generally parallel to the axis of probe body 140. Due to the swivel mount, electrode assembly 144 is able to maintain apposition to the tissue during vaporization. Such a configuration is particularly advantageous in allowing for lateral, anterior/posterior access.

Figure 17:
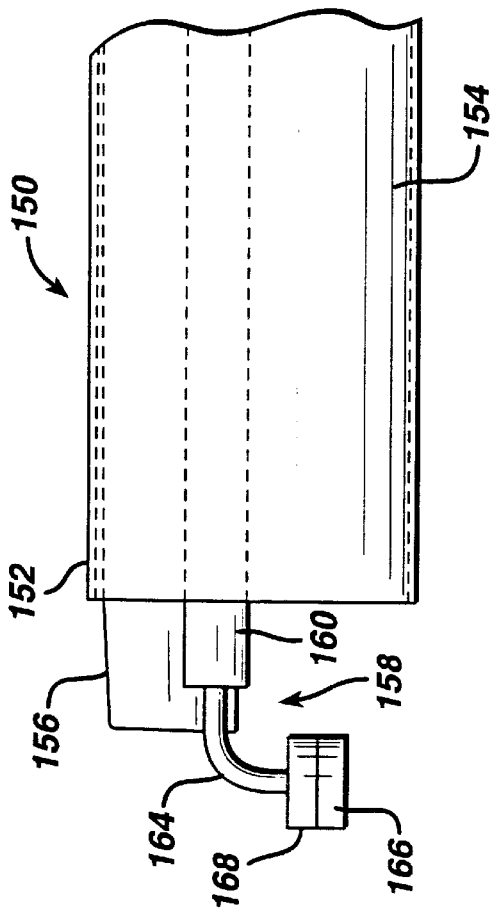
FIG. 17 is a side view of another embodiment of an electrosurgical device according to the invention.

Referring now to FIGS. 17 and 18, an alternative embodiment of an electrosurgical device 150 will be described. For convenience of discussion, only a distal end 152 of a probe body 154 is shown. Device 150 includes an imaging scope 156 and an electrode assembly 158. Electrode assembly 158 comprises an elongate shaft 160 which includes a conductor which may be coupled to an electrosurgical unit. Coupled to shaft 160 are a pair of arms 162 and 164 to which an electrode 166 having a jacket 168 is coupled. As best shown in FIG. 18, electrode 166 is disposed below scope 156 to provide a clear field of vision for scope 156. As with other embodiments, electrode 166 may be fixedly mounted or pivotally mounted to arms 162 and 164.

Figure 19:
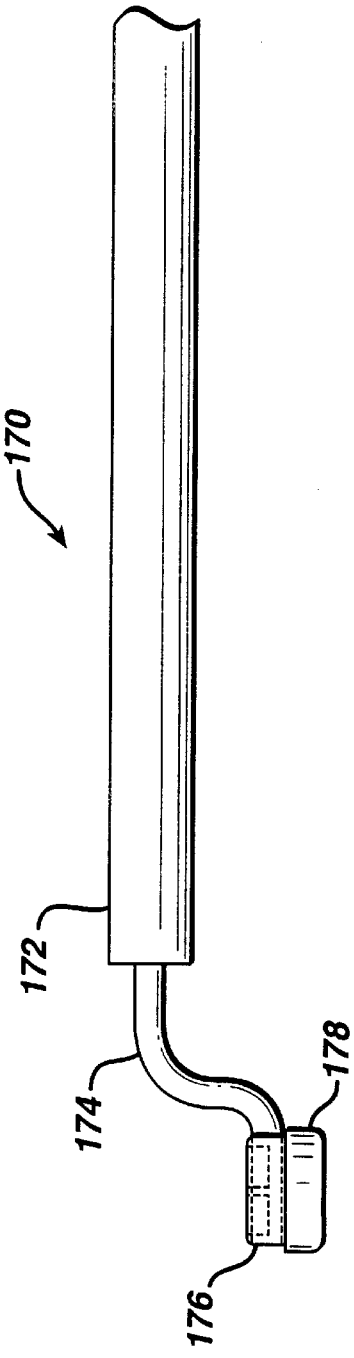
FIG. 19 is a side view of an alternative electrode assembly that may be used with the device of FIG. 17.

Shown in FIG. 19 is an alternative embodiment of an electrode assembly 170 having a shaft 172 and a pair of arms 174 which have a S-shaped configuration. Arms 174 are coupled to a jacket 176 and an electrode 178. The S-shaped configuration of arms 174 provides an alternative way to dispose electrode 178 below the field of vision of the scope.

The invention has now been described in detail for purposes of clarity of understanding. However, it will be appreciated that certain changes and modifications may be made within the scope of the invention. Therefore, the scope and content of the invention are to be determined in light of the appended claims and as well as the full equivalence to which those claims are entitled.

What is claimed is:

1. An electrosurgical probe comprising:
    a probe body having a proximal end, a distal end and at least one lumen; and
    an electrode assembly operably coupled to the distal end, the electrode assembly comprising an electrode constructed of a metal or metal alloy and a jacket constructed of a ceramic disposed to cover at least a portion of the electrode, wherein the jacket and the electrode have a combined mass that is greater than about 0.04 gram to dissipate heat produced during operation of the electrode so that the electrode does not experience material degradation, and wherein the jacket provides insulation between the electrode and a conductive medium such that the electrode is operable in the conductive medium.

2. A probe as in claim 1, wherein the jacket and the electrode have a combined mass that is in the range from about 0.1 gram to about 0.2 gram.

3. A probe as in claim 1, wherein the electrode has an exposed surface area in the range from about 0.007 in$^2$ to about 0.125 in$^2$.

4. A probe as in claim 1, wherein the probe body includes a working lumen, a fluid inflow lumen, and a fluid outflow lumen.

5. A probe as in claim 4, wherein the working lumen is adapted to receive an imaging scope.

6. A probe as in claim 4, wherein the probe body has an outer diameter in the range from about 0.07 inch to about 0.3 inch, and wherein the working lumen has a diameter in the range from about 0.03 inch to about 0.16 inch.

7. A probe as in claim 1, wherein the electrode assembly is coupled to the distal end with a fixed mount such that the position of the electrode assembly relative to the probe body is fixed.

8. A probe as in claim 1, wherein the electrode assembly is coupled to the distal end with a movable mount such that the electrode assembly is movable relative to the probe body.

9. An electrosurgical system comprising:
    a probe body having a proximal end, a distal end and at least one working lumen;
    an electrode assembly operably coupled to the distal end, the electrode assembly comprising an electrode and a jacket disposed to cover at least a portion of the electrode, wherein the jacket and the electrode have a combined mass sufficient to dissipate heat produced during operation of the electrode so that the electrode does not experience material degradation, and wherein the jacket provides insulation between the electrode and a conductive medium such that the electrode is operable in the conductive medium; and an imaging scope receivable in the working lumen.

10. A system as in claim 9, further comprising an electrosurgical unit to supply current to the electrode.

11. A system as in claim 9, wherein the probe body includes a fluid inflow lumen and a fluid outflow lumen.

12. A system as in claim 11, further comprising a source of conductive fluid which is connectable to the fluid inflow lumen and a vacuum source connectable to the fluid outflow lumen.

13. A system as in claim 9, wherein the electrode is constructed of a metal or metal alloy, and wherein the jacket is constructed of a ceramic.

14. A system as in claim 13, wherein the jacket and the electrode have a combined mass that is greater than about 0.04 gram.

15. A system as in claim 14, wherein the jacket and the electrode have a combined mass that is in the range from about 0.1 gram to about 0.2 gram.

16. A system as in claim 9, wherein the electrode has an exposed surface area in the range from about 0.007 in$^2$ to about 0.125 in$^2$.

17. A system as in claim 9, wherein the probe body has an outer diameter in the range from about 0.07 inch to about 0.3 inch, and wherein the working lumen has a diameter in the range from about 0.03 inch to about 0.16 inch.

18. A system as in claim 9, wherein the electrode assembly is coupled to the distal end with a fixed mount such that the position of the electrode assembly relative to the probe body is fixed.

19. A system as in claim 9, wherein the electrode assembly is coupled to the distal end with a movable mount such that the electrode assembly is movable relative to the probe body.

20. A method for electrosurgically treating tissue, the method comprising:

providing an electrosurgical probe comprising a probe body having a proximal end, a distal end, at least one lumen, and an electrode assembly operably coupled to the distal end, the electrode assembly comprising an electrode and a jacket disposed to cover at least a portion of the electrode;

introducing the probe into a body cavity;

introducing a conductive medium into the cavity through the lumen;

introducing an imaging scope into the lumen and visualizing the positioning of the electrode with the imaging scope;

supplying current to the electrode; and positioning the electrode near or against tissue to treat the tissue, wherein the jacket provides insulation between the electrode and the conductive medium, and wherein heat produced during treatment of the tissue is dissipated by the jacket and the electrode to prevent the electrode from materially degrading.

21. A method as in claim 20, further comprising operating the electrode at a power setting in the range from about 40 Watts to about 400 Watts to vaporize the tissue.

22. A method as in claim 20, wherein the probe body includes an aspiration lumen, and further comprising withdrawing the conductive medium from the body cavity through the aspiration lumen.

23. A method as in claim 20, wherein the electrode assembly is pivotally coupled to the distal end, and further comprising moving the electrode along tissue, with the electrode assembly pivoting to accommodate the shape of the tissue.

24. A method as in claim 20, wherein the electrode is constructed of a metal or metal alloy, wherein the jacket is constructed of a ceramic, and wherein the jacket and the electrode have a combined mass that is greater than about 0.04 gram to dissipate the heat.

25. A method as in claim 24, wherein the jacket and the electrode have a combined mass that is in the range from about 0.1 gram to about 0.2 gram to dissipate the heat.

* * * * *